United States Patent
Sakaguchi et al.

(10) Patent No.: US 8,733,557 B2
(45) Date of Patent: May 27, 2014

(54) SUBSTRATE AND METHOD FOR PRODUCTION THEREOF

(75) Inventors: Hirokazu Sakaguchi, Otsu (JP); Hiroshi Takahashi, Otsu (JP); Yoshiyuki Ueno, Otsu (JP); Hiroyuki Sugaya, Otsu (JP)

(73) Assignee: TORAY Industries, Inc., Tokyo (JP)

( * ) Notice: Subject to any disclaimer, the term of this patent is extended or adjusted under 35 U.S.C. 154(b) by 732 days.

(21) Appl. No.: 12/310,994

(22) PCT Filed: Sep. 13, 2007

(86) PCT No.: PCT/JP2007/067784
§ 371 (c)(1),
(2), (4) Date: Feb. 1, 2010

(87) PCT Pub. No.: WO2008/032758
PCT Pub. Date: Mar. 20, 2008

(65) Prior Publication Data
US 2010/0176048 A1    Jul. 15, 2010

(30) Foreign Application Priority Data

Sep. 15, 2006 (JP) .................................. 2006-250459
Feb. 28, 2007 (JP) .................................. 2007-048839

(51) Int. Cl.
*A61L 33/00* (2006.01)
*B01D 63/00* (2006.01)

(52) U.S. Cl.
USPC ................ 210/500.24; 210/321.62; 210/636; 427/2.13

(58) Field of Classification Search
USPC ........ 210/321.62, 321.69, 636; 427/2.3, 2.11, 427/2.12, 2.13; 424/486
See application file for complete search history.

(56) References Cited

U.S. PATENT DOCUMENTS

| | | | | |
|---|---|---|---|---|
| 5,658,466 A | * | 8/1997 | Kawaguchi et al. | 210/636 |
| 6,265,016 B1 | * | 7/2001 | Hostettler et al. | 427/2.11 |
| 7,815,802 B2 | * | 10/2010 | Wen et al. | 210/635 |
| 2003/0129130 A1 | * | 7/2003 | Guire et al. | 424/1.11 |

* cited by examiner

*Primary Examiner* — Tony G Soohoo
*Assistant Examiner* — Peter Keyworth
(74) *Attorney, Agent, or Firm* — Kubovcik & Kubovcik (57) ABSTRACT

The present invention relates to a substrate including a compound having blood anticoagulation activity and a hydrophilic polymer compound, wherein the amount of elution of the compound having blood anticoagulation activity is less than 0.6 μg/ml, and a manufacturing method of a substrate, wherein after a compound having blood anticoagulation activity and a hydrophilic compound brought in contact with a substrate are irradiated with radiation, unreacted components are washed out.

2 Claims, 3 Drawing Sheets

SUBSTRATE AND METHOD FOR PRODUCTION THEREOF

This application is a 371 of international application PCT/JP2007/067784, filed Sep. 13, 2007, which claims priority based on Japanese patent application Nos. 2006-250459 and 2007-048839 filed Sep. 15, 2006, and Feb. 28, 2007, respectively, which are incorporated herein by reference.

TECHNICAL FIELD

The present invention relates to a substrate and a surface modification technology thereof suitably used in a medical field.

BACKGROUND ART

Blood has properties of being activated and thrombus being formed therein when it is brought into contact with foreign matter. If thrombus is formed in a circuit or dialyzer in an extracorporeal circulation of blood such as an artificial kidney, circulating pressure rises and in addition to becoming impossible for blood to circulate shortly, there is a risk of the blood vessel being obstructed if a portion of generated thrombus enters the body. Therefore, it is necessary to add a blood anticoagulation activity (anti-coagulability) substance and this is a method widely used. Inexpensive heparin is generally used as the anti-coagulability substance. However, heparin cannot be used for patients of heparin-induced thrombocytopenia (hereinafter, referred to as HIT) and patients with bleeding such as those immediately after an operation and an expensive anticoagulant such as nafamostat mesilate and gabexate mesilate needs to be used instead, leading to a problem of rising medical expenses (See Non-patent Documents 1, 2, and 3).

Research on anti-coagulability materials that can reduce usage of anticoagulants by imparting anti-coagulability to the surface of material or can be used under conditions of no added anticoagulant has been conducted. That is, such materials are obtained by immobilizing anti-coagulable substances on the surface of material and include a heparinized material as the most researched material. The main method of immobilizing heparin to a material is based on an ionic bond using cations of ammonium salt and the like introduced into the material and anions of heparin (See Non-patent Document 4). However, in this case, heparin is likely to elute and thus, this method cannot be used for patients with HIT and also has a problem of lowered anti-coagulability. Therefore, several methods of immobilizing heparin based on a covalent bond have been reported to resolve the problem of elution. First, an immobilization method based on the covalent bond formed organic chemically has been reported, but has a problem of lowering anti-coagulability during chemical reaction (See Patent Document 1). Second, a method of immobilizing heparin on a material based on the covalent bond while preventing anti-coagulability from being lowered by using an ion beam and laser light has been reported, but since an ion beam and laser light are used, it is difficult to immobilize heparin in a portion such as the surface inside a hollow fiber where a shadow is cast by an ion beam (See Patent Document 2).

Heparin itself has very low anti-coagulability and expresses high anti-coagulability by being bound to antithrombin III (hereinafter, referred to as ATIII). That is, there is also a problem that anti-coagulability is insufficient in ATIII deficient blood (See Non-patent Document 2).

With respect to the above problems of heparin immobilization material, research on materials on which compounds having anti-coagulability other than heparin are immobilized has been conducted (See Patent Document 3). However, there is a problem that it is difficult to suppress platelet attachment by a compound having anti-coagulability alone, leading to formation of platelet thrombosis. In addition, no proposal has been made regarding the problem of elution of a compound having anti-coagulability from substrate.

In recent years, research on immobilization of a compound having anti-coagulability other than heparin by radiation has been conducted (See Patent Document 4). By using this method, a lowering of anti-coagulability with radiation irradiation can be suppressed and further, elution of the compound having anti-coagulability from the substrate can be said to be reduced to a certain extent. However, according to the method of immobilizing only the compound having anti-coagulability, an intrinsic blood-clotting reaction can be suppressed, but it is difficult to suppress platelet attachment so that a sufficient level of anti-coagulability has not yet been achieved. Moreover, non-reactants during radiation irradiation are not taken into account here and the lowering of elution of the compound having anti-coagulability from the substrate cannot have been reduced.

Patent Literature 1: JP-A-H2003-507082
Patent Literature 2: JP-A-H2001-213984
Patent Literature 3: JP-A-H2004-525888
Patent Literature 4: JP-A-H2006-291193
Non-Patent Literature 1: Kazuo Ota, "Jinkoujinzounojissai (in revised form 4)", Nankodo, 1993, pp 158-164
Non-Patent Literature 2: Tetsuzo Agishi et al. "Tousekinyumon", Syujunsha, 1994, pp. 170-182
Non-Patent Literature 3: American journal of hematology. 2006 81 (1), pp. 36-44
Non-Patent Literature 4: Journal Biomedical Materials Research. 1998 39, pp. 86-91

DISCLOSURE OF THE INVENTION

Problem to be Solved by the Invention

In view of the above problems, an object of the present invention is to provide a substrate to which anti-coagulability, preferably antithrombin activity and platelet attachment suppressive ability are imparted and which is excellent in blood compatibility and a manufacturing method such a substrate and further, to be able to reduce the amount of elution of a compound having anti-coagulability and a hydrophilic polymer compound.

1. A substrate, comprising a compound having blood anticoagulation activity and a hydrophilic polymer compound, wherein the amount of elution of the compound having blood anticoagulation activity is less than 0.6 µg/ml.

2. The substrate according to 1, wherein 1 ng/cm$^2$ or more of the compound having blood anticoagulation activity is contained on the substrate surface.

3. The substrate according to 1 or 2, wherein the compound having blood anticoagulation activity has antithrombin activity and the amount of thrombin adsorption is 1.0 ng/cm$^2$ or more.

4. The substrate according to anyone of 1 to 3, wherein the number of attached platelets is $10/(4.3 \times 10^3 \, \mu m^2)$ or less and a blood coagulation time is extended by 10 seconds or more when a blood coagulation test is performed.

5. The substrate according to any one of 1 to 4, wherein abundance of the hydrophilic polymer compound is 20% by weight or more.

6. The substrate according to any one of 1 to 5, wherein the compound having blood anticoagulation activity contains a blood anticoagulation activity portion and a polymer chain portion.

7. The substrate according to 6, wherein the polymer chain portion has hydrophilicity.

8. The substrate according to 7, wherein the polymer chain portion contains at least one selected from a propylene glycol residue, a polyvinyl pyrolidone residue, a polypropylene glycol residue, a polyvinyl alcohol residue, and a residue of a copolymer of one residue thereof.

9. The substrate according to 8, comprising the polyvinyl alcohol whose saponification degree is 50 mol % or more and 99.9 mol % or less.

10. The substrate according to any one of 7 to 9, wherein a compound having the blood anticoagulation activity is 4-methoxy-benzenesulfonyl-Asn (PEG2000-Ome)-Pro-4-amidinobenzylamido.

11. The substrate according to any one of 1 to 10, wherein the hydrophilic polymer compound contains at least one selected from a group consisting of polyvinyl alcohol, polyether, polyvinyl pyrolidone, and a material composed of polyether and polysiloxane.

12. The substrate according to 11, wherein the material composed of polyether and polysiloxane is a polyether/polysiloxane copolymer.

13. The substrate according to 11 or 12, wherein the polyether includes polyethylene glycol and polypropylene glycol.

14. The substrate according to 12 or 13, wherein content of polypropylene glycol in the polyether/polysiloxane copolymer is 5 mol % or more and 90 mol % or less.

15. A manufacturing method of a substrate, wherein after a compound having blood anticoagulation activity and a hydrophilic compound brought in contact with a substrate are irradiated with radiation, unreacted components are washed out.

16. The manufacturing method of a substrate according to 15, wherein after the compound having blood anticoagulation activity and the hydrophilic polymer compound brought in contact with the substrate are irradiated with radiation, the substrate is cleaned by a surface active agent.

17. The manufacturing method of a substrate according to 15 or 16, wherein when the compound having blood anticoagulation activity and the hydrophilic compound brought in contact with the substrate are irradiated with radiation, the substrate is irradiated with radiation while containing an organic solvent solution satisfying following conditions A and B:

A: Moisture content is 25% by volume or more and 90% by volume or less;

B: At least one secondary or tertiary hydroxyl group is contained.

18. The manufacturing method of a substrate according to any one of 15 to 17, wherein when the compound having blood anticoagulation activity and the hydrophilic polymer compound brought in contact with the substrate are irradiated with radiation, the substrate is irradiated with radiation while containing a buffer solution of pH 3 or more and 10 or less.

Effect of the Invention

According to the present invention, extremely high anti-coagulability can be imparted to the substrate surface by introducing a compound having anti-coagulability and a hydrophilic polymer compound to the substrate surface. As a result, usage of anticoagulants added to blood during extra-corporeal circulation can be reduced also for uses in which blood and material are brought into contact and such anticoagulants need not be used in some cases and therefore, risks such as adverse reactions to anticoagulants can be reduced and eventually, reduction in medical expenses can be expected.

Moreover, according to the manufacturing method of the present invention, radiation grafting polymerization is performed on the substrate surface by irradiating a compound having anti-coagulability and a hydrophilic polymer compound in contact with a substrate in the presence of an organic solvent with radiation and further, by washing out non-reactants while maintaining activity of the compound having anti-coagulability, so that the risk of the compound having anti-coagulability introduced to the substrate surface being eluted can also be reduced.

EXPLANATION OF SYMBOLS 1 and 1'. blood port
2 and 2'. dialysis port
3. module case
4. hollow fiber
5. potting agent
6. mini-module
7. silicon tube
8. perista pomp
9. polystyrene round tube or EIKEN tube No. 1
10. plasma or protein solution
11. manometer Best Mode For Carrying Out The Invention A substrate according to the present invention contains a compound having anti-coagulability and a hydrophilic polymer compound. If only a compound having anti-coagulability is introduced to the substrate surface, activation of a blood-clotting reaction by clotting factors can be suppressed, but formation of thrombus and attachment of platelets to the substrate cannot be completely suppressed in uses in which blood is brought into contact because aggregation of platelets cannot be suppressed. If, on the other hand, only a hydrophilic polymer compound is introduced to the substrate surface, aggregation of platelets can be suppressed, but activation by clotting factors can be suppressed and thus, like the above case, formation of thrombus and the like cannot be completely suppressed. That is, the subject of the present invention cannot be resolved simply by increasing the amount of one compound. In the present invention, however, only after a substrate being caused to contain both a compound having anti-coagulability and a hydrophilic polymer compound, a plurality of coagulation reactions can be suppressed and a strong anti-coagulability material becomes creatable. Further, in the present invention, elution of a compound having anti-coagulability is taken into consideration because elution of the compound having anti-coagulability in blood has an effect of delaying the coagulation time and may cause adverse reactions. By reducing the amount of elution to less than 1 µg/ml, preferably to less than 0.8 µg/ml, more preferably to less than 0.6 μg/ml, it becomes possible to reduce adverse reactions due to a compound having anti-coagulability and the amount of introduction into the substrate and to achieve safety and lower costs, leading to the solution of the subject of the present invention.

In the present invention, a substrate containing a compound having anti-coagulability and a hydrophilic polymer compound on the substrate surface is a substrate on which surface a compound having anti-coagulability and a hydrophilic polymer compound are present. A compound having anti-coagulability and a hydrophilic polymer compound may or may not be directly coupled. However, it is preferable that these compounds be directly coupled because accordingly these compounds become less likely to be eliminated to be able to continue to have an effect and a reduction in elution of these compounds can be expected. The coupling in this case includes a chemical bond such as a covalent bond, ionic bond, hydrogen bond, coordinate bond, and hydrophobic interaction and the covalent bond is preferable because the covalent bond is a relatively strong bond. Alternatively, the coupling may a combination of a plurality of these bonds. The method of forming a covalent bond, that is, performing grafting of a compound having anti-coagulability and a hydrophilic polymer compound to the substrate surface includes an organic chemical method by a nucleophilic substitution reaction and the like and a radiation chemical method by irradiation with ionizing radiation. Among these methods, the radiation chemical method is preferable because the amount of reaction byproducts is smaller and also the substrate can be sterilized by suitably selecting the type and dose of radiation. The compound having anti-coagulability and a hydrophilic polymer compound may be treated simultaneously or separately. A hydrophilic polymer compound may serve as a component constituting the substrate by being kneaded together with raw material when the substrate is produced, but depending on the type of substrate, mechanical or chemical properties (for example, strength, brittleness, surface charge, and surface wettability) of the substrate may be damaged. Therefore, in such a case, the hydrophilic polymer compound may be introduced and immobilized on the substrate surface, for example, by directly bringing an aqueous solution containing the hydrophilic polymer compound into contact with the substrate surface. By adopting such an introduction/immobilization method, the scope of applicability is increased without the need to select the type of substrate. Therefore, it becomes possible not only to make use of an effect of the present invention in many fields, but also to easily change the type of hydrophilic polymer compound so as to optimize the substrate for the use, which is more suitable in terms of functionality and production costs.

The method of confirming eluted substances is not specifically restricted, but a method of measurement described below is cited as an example. For example, an ECA-T kit available from HaemoSys is used as a reagent and COATRON M1 (code 80 800 000) manufactured by TECO Medical Instruments Production as an apparatus. An area (for a hollow fiber, a surface area inside the fiber that comes into contact with blood) (hereinafter, referred to as an area A) that comes into contact with blood, biogenic substance, or body tissue is washed with 160 μl of human plasma per 1 cm$^2$ for four hours. 80 μl of human plasma after cleaning is collected and 20 μl of distilled water is added thereto. This solution is defined as a sample solution. Immediately after the sample solution is prepared, 100 μl of ECA prothrombin buffer, 30 μl of sample solution, and 25 μl of ECA-T substrate are mixed and set, after being incubated at 37° C. for 60 s, to the apparatus. Then, 50 μl of ECA ecarin reagent is added for measurement. A mixed solution of 20 μl of aqueous solution of a compound having anti-coagulability or blank distilled water and 80 μl of human plasma is measured in advance by the same technique, the result thereof is used as a calibration curve, and the amount of compound having anti-coagulability calculated from the calibration curve is defined as the amount of elution.

The amount of compound having anti-coagulability on the substrate surface changes depending on the strength of anti-coagulability, but if the amount of compound is too small, there is a problem that the effect of anti-coagulability is low. Thus, with reference to the area A, the amount of compound is preferably 0.1 ng/cm$^2$ or more, more preferably 0.5 ng/cm$^2$ or more, still more preferably 1 ng/cm$^2$ or more, and most preferably 50 ng/cm$^2$ or more. If, on the other hand, the amount of compound having anti-coagulability is too large, there is a problem such as increased costs and elution. Thus, the amount of compound is preferably 100 μg/cm$^2$ or less, more preferably 10 μg/cm$^2$ or less, and most preferably 1 μg/cm$^2$ or less. The amount of compound having anti-coagulability on the substrate surface is measured in the following manner: on the basis of loadings of the compound having anti-coagulability with respect to the substrate, the amount of compound is determined in a subsequent process, for example, which is mainly a cleaning process, by subtracting the amount removed by the process to remove unreacted components that are not immobilized on the substrate, but the method is not limited thereto. Also, the amount of compound can be calculated from the calibration curve of the compound having anti-coagulability prepared in advance and the amount of thrombin adsorption by measuring the amount of thrombin adsorption described below.

A compound having anti-coagulability preferably has anti-thrombin activity. A compound having antithrombin activity in the present invention is a compound that suppresses activity of thrombin, which is a coagulation related substance in blood. The amount of thrombin adsorption is measured by enzyme-linked immunosorbent assay (ELISA method), but the method is not limited thereto. A detailed experimental method will be described later and the amount of thrombin adsorbed by the substrate in the present invention is, with reference to the area A, preferably 0.5 ng/cm$^2$ or more and more preferably 1.0 ng/cm$^2$ or more.

Also, if the amount of hydrophilic polymer compound is too small, there is a problem that the effect of suppressing platelet attachment is low. A substrate in the present invention preferably has 20% by weight or more of surface hydrophilic high molecular weight. Here, the surface hydrophilic high molecular weight is defined, if the weight of monomer unit of hydrophilic polymers (number of moles of monomer unit × molecular weight of monomer unit) on the substrate surface is (A) and the weight of monomer unit of polymers (number of moles of monomer unit × molecular weight of monomer unit) constituting the substrate on the substrate surface is (B), as a ratio represented by A/(A+B). The surface hydrophilic high molecular weight is a parameter representing the degree of hydrophilicity on the substrate surface.

The surface hydrophilic high molecular weight is determined by measuring only the substrate surface, that is, up to the depth of about 10 nm from the surface by the X ray photoelectron spectroscopy (ESCA) (the angle of a detector with respect to the incidence angle of X rays is 90 degrees). That is, the surface hydrophilic high molecular weight is determined from changes of area strength of C1s and O1s spectra before and after treatment of the substrate. The surface hydrophilic high molecular weight is preferably 20% by weight or more and more preferably 32% by weight. If the surface hydrophilic high molecular weight is less than 20% by weight, an effect of suppressing attachment of organic matter such as proteins and biogenic substances is lowered.

The substrate of the present invention has $10/(4.3\times10^3 \mu m^2)$ or less of human platelets attached. The number of attached platelets is a value determined as the number of platelets attached to the substrate surface per $4.3\times10^3 \mu m^2$ on the substrate surface when the substrate and blood are maintained in contact with each other for one hour. The measuring method of the amount of attached platelets to be used is as follows: after a sample is shaken in heparin added human blood at 37° C. for one hour, the sample is cleaned by physiological saline, blood components are immobilized by a glutaraldehyde solution, and after slow cleaning and drying (drying under reduced pressure is applied until the rate of change in weight is within 2% before and after drying for one hour), the surface of the sample is observed under 1500× magnification of a scanning electron microscope, the number of platelets in one field of view ($4.3\times10^3 \mu m^2$) is counted, and the average number of numbers of platelets in 10 different fields of view near the center of sample is adopted as the number of attached platelets (numbers/$4.3\times10^3 \mu m^2$). If the amount of attached human platelets exceeds $10/(4.3\times10^3 \mu m^2)$, blood compatibility will be insufficient and also the effect of suppressing attachment of organic matter such as proteins and biogenic substances will be insufficient.

Further, the substrate of the present invention preferably extends the blood coagulation time by 10 seconds or more when a blood coagulation experiment is performed. Here, the blood coagulation time is measured by using Sonoclot (coagulation & platelet function analyzer manufactured by US Sienco Inc.), but the apparatus is not limited to this. Here, physiological saline is added so that the concentration of the substrate becomes 100 μg/ml, 342 μl of human blood and 14.8 μl of calcium gluconate injection solution (available from Dainippon Sumitomo Pharma Co., Ltd.) are added and the extension time is measured by using a SonACT kit and an ACT program, which is an internal program of Sonoclot. The extension time of blood coagulation is preferably 10 seconds or more and more preferably 15 second or more.

A compound having an amino acid as a component can be cited as an example of compound having anti-coagulability used in the present invention. The amino acid has various functional groups as side chains and is suitably capable of expressing activity by the amino acid itself and linking to active groups. A compound having an amino acid as a component is a compound having an α-amino acid constituting proteins and includes, for example, a compound composed of only amino acids such as proteins and peptide and that composed of amino acids and other components other than amino acids such as glycoprotein, amino acid complex, and aminoacyl adenylate.

When blood comes into contact with foreign matter, clotting components are activated to form thrombus shortly. If thrombus is formed in a circuit or dialyzer in an extracorporeal circulation of blood such as an artificial kidney, circulating pressure in blood rises and in addition to becoming impossible for blood to circulate shortly, there is a risk of the blood vessel being obstructed if a portion of formed thrombus enters the body. Therefore, in an extracorporeal circulation of blood, it is necessary to add a compound having anti-coagulability to blood circulating extracorporeally. However, if a compound having the anticoagulation action is added to blood of patients immediately after an operation or those complicated by digestive tract bleeding, such patients may be accompanied by bleeding. Thus, by immobilizing a compound having anti-coagulability on the substrate surface used for extracorporeal circulation, it becomes possible to suppress blood coagulation without adding a compound having anti-coagulability against blood to blood circulating extracorporeally.

A compound having anti-coagulability is a compound that extends the prothrombin time by 30% or more when the compound is added to blood in such a way that the concentration thereof becomes 10 μg/mL, as compared to that when not being added to blood. The prothrombin time can be measured according to a method described in the following literature:

M. Kanai et al. "Rinsho Kensaho Teiyo (Clinical Examination Method Handbook) 30th Ed." Kanehara & Co., Ltd., 1993, pp. 416-418

That is, specifically, 10% by volume of 3.2% sodium citrate and 90% by volume of blood are mixed, 0.1 mL of preparatively isolated citrate plasma is put into a small test tube (inside diameter: 8 mm; length: 7.5 cm), and the test tube is introduced into a constant temperature bath at 37° C. to heat the test tube for about three minutes. 0.2 mL of a tissue thromboplastin/calcium reagent kept at the same temperature is added thereto and at the same time, a stop watch is started and after the small test tube is shaken slightly, the time until fibrin is deposited is measured while the small test tube being settled and tilted.

The compound having anti-coagulability used in the present invention includes, for example, heparin, nafamostat mesilate, sodium citrate, sodium oxalate, α1 antitrypsin, α2 macroglobulin, C1 inhibitor, thrombomodulin, and protein C. Among compounds having anti-coagulability, there is a compound exhibiting a strong blood anticoagulation action by suppressing activity of thrombin, that is, a compound having antithrombin activity.

As compounds having antithrombin activity against ultra-pure water, 4-methoxy-benzenesulfonyl-Asn(PEG2000-Ome)-Pro-4-amidinoben zylamido (hereinafter, sometimes abbreviated as a compound A) shown by the following general formula

[Chem. 1]

(wherein, PEG represents a polyethylene glycol (hereinafter, referred to as PEG) residue of number average molecular weight 2000 and Me represents a methyl group), ATIII and hirudin can be cited.

If a compound having anti-coagulability contains a polymer chain portion like the compound A, the compound can be bound to the substrate in the polymer chain portion so that an anti-coagulable portion can preferably be bound to the substrate to suppress the lowering of activity. A polymer chain portion in the present invention refers to a molecular chain in which a repeating unit having a specific chemical structure is bound by the covalent bond and whose molecular weight is 1000 or more. Such a polymer chain portion includes a hydrophilic polymer chain such as a PEG residue, polyvinyl pyrolidone (hereinafter, referred to as PVP) residue, polypropylene glycol (hereinafter, referred to as PPG) residue, polyvinyl alcohol (hereinafter, referred to as PVA) residue, and a residue of copolymer of one of these. A compound having such a hydrophilic polymer chain can particularly preferably be used because water solubility of a compound having anti-coagulability is less likely lowered, derivatives having an amino group or carboxyl group are marketed, and a method of manufacturing a compound having anti-coagulability by introducing these derivatives into a polymer chain portion is relatively easy.

A hydrophilic polymer compound in the present invention refers to a polymer compound that is soluble in water, or not soluble in water, but can interact weakly with water molecules through an electrostatic interaction or hydrogen bond. A polymer compound refers to a compound whose number average molecular weight is 1000 or more. Examples of the hydrophilic polymer compound include, for example, PVA, PVP, PEG, PPG, material composed of polyether and polysiloxane, polyethylene amine, polyallyl amine, polyvinyl amine, polyvinyl acetate, polyacrylic acid, and polyacrylamide and also a copolymer or graft polymer of a monomer of these polymers and another monomer, but are not limited thereto. Among them, a hydrophilic polymer compound containing at least one of the material composed of polyether and polysiloxane, PVA, polyether, and PVP is suitably used and particularly, the material composed of polyether and polysiloxane and PVA achieve a high hydrophilic effect and are preferable. The material composed of polyether and polysiloxane used herein includes a copolymer of polyether and polysiloxane, polymer complex, and polymer blended material. Among them, the copolymer is preferable because the copolymer is highly soluble in water and thus, graft treatment by an aqueous solution is possible so that risks of ignition to solvent and combustion in facilities of radiation irradiation can be reduced. The polyether/polysiloxane copolymer is composed of a polyether unit and a polysiloxane unit and a copolymer form thereof may be a random copolymer, block copolymer or graft copolymer or a mixture of these copolymers.

PPG and PEG are suitably used as polyether, but when compared with PEG, PPG is preferable because it has higher hydrophobicity and thus, can have a stronger hydrophobic interaction with the substrate and if, for example, radiation grafting is performed, a material composed of polyether and polysiloxane can efficiently be grafted to the substrate. Herein, if content of PPG in polyether increases too much, solubility of the copolymer in water lowers and thus, content of PPG in polyether is preferably 5 mol % or more, more preferably 10 mol % or more, and still more preferably 20 mol % or more. On the other hand, content of PPG in polyether is preferably 90 mol % or less, more preferably 80 mol % or less, and still more preferably 60 mol % or less. The content (mol %) of PPG in the present invention is calculated according to the formula (1).

$$P = 100 \times (a)/(b) \quad \text{formula (1)}$$

In the formula, P is the content (mol %) of PPG, (a) is the number of PPG units in polyether, and (b) is the number of ether units in polyether. A PPG unit in polyether refers to a structure represented by the following chemical formula:

[Chem. 2]

An ether unit in polyether refers to a structure represented by the following chemical formula:

[Chem. 3]

In the above formula, $R_1$ is an alkyl group having six carbon atoms or less. PPG content can be measured by the nuclear magnetic resonance spectroscopy (hereinafter, referred to as $^1$H-NMR) or the like.

Moreover, polyether may be copolymerized and PEG is preferably used as another copolymerization component other than PPG in polyether from the viewpoint of ease of availability. In a material composed of such PEG and PPG, other copolymerization components may be contained to such an extent that an effect thereof is not undermined.

Regarding PVA as a polymer chain portion of a compound having anti-coagulability or PVA as a hydrophilic polymer compound, PVA having a low saponification degree is preferable because it has an effect of further making the substrate more hydrophilic. The saponification degree here is a value determined by the formula (4). Herein, if the saponification degree is too low, solubility in water becomes extremely low and thus, it may be difficult to treat the substrate surface. Therefore, the saponification degree is preferably 50 mol % or more, more preferably 74 mol % or more, and still more preferably 78 mol % or more. Conversely, if the saponification degree is too high, solubility in water also becomes lower, which results in requiring heating during dissolution and leading to lower productivity, and thus, a too high saponification degree is not preferable. Therefore, the saponification degree is preferably 99.9 mol % or less, more preferably 95 mol % or less, and still more preferably 90 mol % or less.

[Chem. 4]

formula (2)

[Chem. 5]

formula (3)

$(k) = (m)/((n) + (m)) \times 100$ formula (4)

Symbols in the formula (4) are as follows:
(k): Saponification degree
(m): Number of monomer repeating units represented by the formula (2) in PVA (n): Number of monomer repeating units represented by the formula (3) in PVA The manufacturing method of a substrate of the present invention uses a method by which a compound having anti-coagulability and a hydrophilic polymer compound in contact with a substrate are irradiated with radiation. In a preferable aspect of the manufacturing method of a substrate of the present invention, a method of irradiating these compounds in contact with the substrate in the presence of an organic solvent with radiation is used.

Radiation used in the present invention is a particle beam or an electromagnetic wave of high energy and such radiation includes, for example, α ray, β ray, γ ray, X ray, ultraviolet ray, electron beam, and neutron beam. Among them, γ ray and electron beam are preferably used in that energy is particularly high and the substrate can efficiently be modified. γ ray, X ray, and electron beam are suitable for modification of the substrate such as a medical material because the substrate can be sterilized at the same time by controlling the dose.

When the substrate is irradiated with radiation, if the dose of radiation is too small, it becomes difficult to control the dose such as variability in absorbed dose in the substrate. Thus, the dose of radiation is preferably 1 kGy or more and more preferably 5 kGy. If sterilization is performed simultaneously with modification for a substrate such as a medical material, the dose of radiation is preferably 10 kGy or more and more preferably 20 kGy. Herein, irradiation with an excessive dose of radiation deteriorates the substrate itself and thus, the dose of radiation is preferably 5000 kGy or less, more preferably 1000 kGy or less, and still more preferably 100 kGy or less.

If activity of a compound having anti-coagulability lowers due to radiation irradiation, a lowering of activity thereof can be prevented by an organic solvent. That is, a substrate with which a compound having a blood anticoagulation activity is brought into contact in the presence of an organic solvent is irradiated with radiation.

An organic solvent suitably used in the present invention includes a solvent containing a hydroxyl group. The hydroxyl group has a great stabilizing effect on radicals generated by radiation irradiation, is a nonionic functional group, has a weak interaction with compounds having strong surface charges, has small oxidizing/reducing power, and causes little denaturalization of compounds. Particularly secondary and tertiary hydroxyl groups have a great stabilizing effect on radicals and thus, in the present invention, an organic solvent having at least one secondary or tertiary hydroxyl group, for example, glycerin, propylene glycol (hereinafter, referred to as PG), isopropanol (hereinafter, referred to as IPA), 2-butanol, 2,3-butanediol, and 1,3-butanediol is used. Herein, since an organic solvent having only primary hydroxyl groups such as EG and ethanol has a small stabilizing effect on radicals and is dangerous if content of a solvent having high ignitability such as ethanol is increased, an organic solvent having only primary hydroxyl groups is not included in organic solvents in the present invention. Moreover, when the sterilization method of compound in the present invention is used for medical material or a manufacture of medical devices containing thereof, safety thereof needs to be considered and therefore, among nonaqueous solvents, those with lower toxicity are suitably used.

The upper limit of moisture content in an organic solvent aqueous solution is 90 vol % and if the moisture content exceeds 90 vol %, a radical stabilizing effect of the organic solvent cannot be sufficiently achieved. In being the range of 90 vol % or less, the more the moisture content, the better. If, on the other hand, the moisture content is low, for example, when used in medical devices, biocompatibility may be influenced by organic solvent residues after cleaning and, in addition, for example, when used for radiation grafting, a lowering of graft efficiency may be considered. Thus, the moisture content is preferably 25 vol % or more to the whole solvent amount and more preferably 50 vol % or more.

In the present invention, dissolution of a compound that is unstable with respect to radiation means dissolution of the compound in the organic solvent into a uniform mixture. Dispersion of a compound that is unstable with respect to radiation means dispersion of the compound in the organic solvent. The concentration of a compound in an organic solvent is not limited, but if the concentration is too high, some types of compound may lose original physical properties of the compound after gelation due to progress of a crosslinking reaction and thus, the concentration of a compound in an organic solvent solution is preferably 50% by weight or less, more preferably 30% by weight or less, and still more preferably 20% by weight or less.

The moisture content in the present invention is defined by the following formula:

(Volume of water contained in a compound unstable with respect to radiation and an organic solvent aqueous solution that dissolves and/or disperses the compound)/(Volume of a compound unstable with respect to radiation and an organic solvent solution that dissolves and/or disperses the compound) ×100(%)

The method that brings a compound having anti-coagulability into contact with the substrate in the presence of an organic solvent includes a method by which a compound having blood anticoagulation activity is dissolved or dispersed in the organic solvent and the substrate is dipped in the obtained liquid or the obtained liquid is applied to the substrate. Here, dissolution of a compound having anti-coagulability means formation of a uniform mixture, that is, a solution after the compound being dissolved in a solvent. Dispersion of a compound having anti-coagulability means dispersion of the compound in a solvent in a colloidal or micelle state. If a compound having anti-coagulability is hard to dissolve in a target organic solvent, after a solution obtained by dissolving the compound having anti-coagulability in a solvent having high solubility with respect to the compound having anti-coagulability being brought into contact with the substrate, the solvent may be replaced by the target organic solvent. In this case, the solvent in which the compound having anti-coagulability is dissolved may be an inorganic solvent such as water. That is, after the substrate being brought into contact with a solution obtained by dissolving a compound having anti-coagulability in water, the water is replaced by an organic solvent and the substrate is irradiated with radiation.

In the present invention, a compound having anti-coagulability may be applied or adsorbed to a substrate in advance, and the substrate to which the compound is attached may be dipped in an organic solvent.

A buffer used for a compound having anti-coagulability and a hydrophilic polymer compound in the present invention is a solution prepared in such a way that pH thereof does not change even if a small amount of acid or base is added and the concentration thereof changes, and includes, for example, a phosphate buffer, tris-hydroxymethyl-aminomethane (hereinafter, referred to as Tris) buffer, a bis (2-hydroxyethyl) imino tris (hydroxymethyl)methane (hereinafter, referred to as Bis-Tris) buffer, an acetate buffer, a citrate buffer, and a borate buffer. Among these buffers, the phosphate buffer, Tris buffer, and Bis-Tris buffer are suitably used because these buffers have a buffer action in neutral and acidic regions and are frequently added as solvents of compounds having physiological activity. Herein, the buffer range is pH 3 or more and preferably 5 or more because under strong acid conditions of pH 3 or less or strong alkali conditions of pH 10 or more, a portion of molecular structure of compounds having physiological activity changes, leading to changes in the physical function, chemical function, or physiological function, and when, for example, a graft immobilizing material is created, performance of the material itself is considered to deteriorate. The upper limit thereof is less than pH 10 and preferably 8 or less. The glass electrode method is used for pH measurement, but the measuring method is not limited thereto as long as pH can be measured with equivalent precision. A solution containing a buffer used in the present invention means an aqueous solution of the buffer or a solution containing other solvents or solutions, but does not mean a solution that changes beyond the pH range of the buffer as a whole solution containing the buffer and is preferably a solution whose pH does not change.

In the present invention, an anti-oxidizing agent may be used in combination when a compound having blood anticoagulation activity and a hydrophilic polymer compound are brought into contact with the substrate. This is because an effect to capture hydroxyl radicals generated by radiation irradiation to suppress denaturation of the compound having anti-coagulability can be expected from the anti-oxidizing agent. The anti-oxidizing agent used herein is a compound having molecules with properties more likely to donate electrons to other molecules and also has properties to suppress denaturation of the substrate, and also a compound having molecules with properties to prevent the substrate, the compound having blood anticoagulation activity, and the hydrophilic polymer compound from getting denatured due to radiation.

Examples of anti-oxidizing agent include water soluble vitamins such as vitamin C; polyphenols; mineral salts such as sodium hydrosulfite, sodium pyrosulfite, and sodium dithionate; uric acid; cystein; and glutathione, but not limited thereto. These anti-oxidizing agents are used alone or two or more kinds thereof are used in combination.

Since it is necessary to consider safety when the substrate according to the present invention is used in medical devices, an anti-oxidizing agent with lower toxicity is used. The concentration of an anti-oxidizing agent depends on the type of the contained anti-oxidizing agent and the dose of radiation irradiation and thus, an optimal concentration may be used according to circumstances.

In order to reduce the amount of elution of the compound having anti-coagulability and hydrophilic polymer compound after these compounds being imparted to the substrate surface, the substrate may be washed before, after, or both before and after radiation irradiation. Since the compound having anti-coagulability and hydrophilic polymer compound are linked to the substrate surface through covalent bonds particularly after radiation irradiation, there is little risk that the compound having anti-coagulability and hydrophilic polymer compound are excessively removed even by excessive cleaning. Further, unreacted components and byproducts can be removed by cleaning and thus, the substrate can be used particularly for medical uses without anxiety. Water, physiological saline, pH buffer, or an organic solvent can be used for cleaning. A solution of a surface active agent achieves a high cleaning effect.

The surface active agent in the present invention means a general surface active agent and is a substance that exhibits strong surface activity with respect to water and has both a hydrophilic portion and a hydrophobic (lipophilic) portion in its molecule. When a substrate having an ionic functional group or a hydrophilic polymer compound is used, if an ionic surface active agent among surface active agents is used, the possibility of physical properties of surface being changed by linkage of the surface active agent due to an electrostatic interaction cannot be denied. Thus, a nonionic surface active agent is preferably used. Among nonionic surface active agents, polyoxyethylene alkylphenylether and polyoxyethylene alkylether are particularly excellent in cleaning effect.

In the present invention, the surface active agent is frequently a solid or a viscous liquid and when used for cleaning, the surface active agent is preferably a liquid in terms of handling properties. If the concentration of solution is too low, a sufficient cleaning effect cannot be achieved and conversely, if the concentration of solution is too high, the substrate could be denatured as well as heightening production costs. Therefore, the concentration of a surface active agent solution is preferably 0.001% by weight or more, more preferably 0.005% by weight or more, and still more preferably 0.01% by weight or more. On the other hand, the upper concentration is preferably 20% by weight or less, more preferably 10% by weight or less, and still more preferably 5% by weight or less.

There may be used any cleaning method of a substrate by which a cleaning agent such as a surface active agent and a solution to which a surface active agent is added is brought into contact with the substrate so that an excessive compound having anti-coagulability and hydrophilic polymer compound are leached. For example, a method of cleaning by which a cleaning agent is passed at a predetermined flow rate in a predetermined direction is most efficient and can clean the substrate well. Also a method of dipping the substrate in a surface active agent may be adopted as the cleaning method. For example, a surface active agent or a solution obtained by adding a surface active agent can be used as a filling liquid of a blood purification module. When a surface active agent or a solution obtained by adding a surface active agent is passed to the substrate in a predetermined direction, the surface active agent or the solution may be circulated around the substrate, but reuse of a surface active agent to which a compound having anti-coagulability, a hydrophilic polymer compound and the like have eluted may lead to deterioration in cleaning efficiency. If the flow rate when a cleaning liquid is passed at a predetermined flow rate for cleaning is too low, a sufficient cleaning effect may not be obtainable. If the flow rate is too high, the cleaning time will be longer, leading to lower productivity. Therefore, the flow rate per surface area of the substrate is preferably 0.5 L/m$^2$ or more, more preferably 1 L/m$^2$ or more, and still more preferably 3 L/m$^2$ or more. On the other hand, the upper limit of the flow rate is preferably 300 L/m$^2$ or less, more preferably 200 L/m$^2$ or less, and still more preferably 100 L/m$^2$ or less.

By further cleaning with water or physiological saline after cleaning the substrate with a surface active agent, the surface active agent can be prevented from remaining on the substrate. The phrase "cleaning with water or physiological saline" means cleaning by using water and physiological saline separately.

By cleaning the substrate before radiation irradiation, the amount of the compound having blood anticoagulation activity and hydrophilic polymer compound that are not grafted can be reduced so that cleaning after radiation irradiation can be reduced.

A polymeric material is preferably used as a substrate used for the present invention. Examples of polymeric compound constituting a polymeric material includes, for example, polymethacrylate such as polymethyl methacrylate (hereinafter, referred to as PMMA), polyacrylate, polypropylene, polyethylene, polyvinyl chloride, polyvinylidene chloride, polyvinylidene fluoride, polyvinyl acetate, polycarbonate, cellulose, cellulose acetate, cellulose triacetate, polyacrylonitrile, polyamide, polysulfone (hereinafter, referred to as PSf), polyether sulfone, polystyrene, polyester, and polyurethane, but not limited thereto.

A substrate of the present invention can suitably be used as a medical substrate. Examples of medical substrate include an artificial vessel, catheter, blood bag, contact lens, intraocular lens, and auxiliary devices for operation, and also a separation film and adsorbent contained and used by a biogenic substance separation module and blood purification module are included. In the present invention, the biogenic substance separation module is a module that separates biogenic substances by filtration, dialysis, adsorption and the like to collect a portion thereof and is not limited to the medical substrate. The blood purification module is a module having a function to remove waste matters and toxic substances by adsorption, filtration, and diffusion when blood is circulated extracorporeally and includes, specifically, an artificial kidney, pre- or post-column thereof, and exotoxin adsorption column.

The form of a separation film contained in a blood purification module is not specifically limited and is used as a flat film or hollow fiber. A hollow fiber generally has a large surface area per treating liquid volume and pressure losses can be minimized so that the method of the present invention can be applied most efficiently. A smaller inside diameter of the hollow fiber is preferable to increase the film surface area per treating liquid volume, and is preferably 1000 μm or less and more preferably 500 μm or less. On the other hand, a flat film has an advantage of being producible easily at low costs. Materials of these films include cellulose, cellulose acetate, polycarbonate, PSf, polyester sulfone, polymethacrylate such as PMMA, polyacrylate, polyamide, polyvinylidene fluoride, polyacrylonitrile, polyester, polyurethane, polystyrene, polyethylene, polypropylene, and material including at least one material selected from a group consisting of these derivatives. Among them, PMMA can be bound to a hydrophilic polymer compound such as PEG through hydrogen bonds and when such a hydrophilic polymer compound is immobilized on the substrate surface through covalent bonds by radiation or the like, immobilization occurs efficiently and thus, PMMA is a suitable material. PSf frequently used in dialyzers in recent years has excellent fractionation characteristics and thus, is a preferable material.

A biogenic substance in the present invention refers to cell, protein, nucleic acid, sugar, and lipin derived living body, or a complex thereof. Also, cells cultured in vitro and genetically modified protein are defined as biogenic substances. Among biogenic substances, the substrate according to the present invention is suitable when blood components, that is, cells such as blood corpuscles and platelets and plasma components such as a plasma protein are treated.

The substrate according to the present invention and the manufacturing method thereof will be described below with reference to Examples, but the present invention is not limited to Examples.

EXAMPLE (Swine Extracorporeal Circulation Experiment)
(1) Circulation Circuit Preparation An artificial kidney blood circuit ("Artificial kidney blood circuit H-102-KTS" marketed by Toray Medical Co., Ltd.) was used, and set in a circuit for pressure measurement and a blood pump ("MedTech Line Flow LF-300" manufactured by MedTech).

Physiological saline (1 L) (manufactured by a plant of Otsuka Pharmaceutical Co., Ltd.) was prepared and passed to the artificial kidney module blood side at a flow rate of 100 ml/min for cleaning for five minutes. Subsequently, the circuit from a blood port on the blood outgoing side was connected to a dialyzing fluid port on the dialyzing fluid incoming side and physiological saline was continuously passed to the artificial kidney module dialyzing fluid side at a flow rate of 100 ml/min for cleaning for 10 minutes. In a case where bubbles and the like could not be sufficiently removed, the dialyzing fluid side was plugged and physiological saline was circulated by being passed to the blood side at a flow rate of 100 ml/min.

(2) Swine Preparation and Test Operation

The weight of the swine to be used for experiment was measured. A miniature pig whose weight was in the range of 11.5 kg or more and 13.5 kg or less was used. 40 mg of pentobarbital sodium anesthesia ("Nembutal injection solution" available from Dainippon Sumitomo Pharma Co., Ltd.) per kg of weight was administered intraperitoneally. After checking the anesthesia state, the swine was fixed to the operating table with the face upward. The cervical part (inner parts of both legs) was shaved by a barber's clipper. After disinfection using ethanol for disinfection and a povidone iodine solution ("Isodine" available from Meiji Seika Kaisha Co., Ltd.), the carotid artery and jugular vein (femoral artery and femoral vein) were cut open, and a catheter ("Atom vein catheter (8Fr)" manufactured by Terumo Corporation) for extracorporeal circulation was inserted and fixed into each of the artery and vein. The catheter was filled by a syringe of 10 ml with heparin saline (5 IU/ml) and plugged. Heparin was used only to fill the catheter upon the catheter being inserted.

(3) Extracorporeal Circulation Start

A connector on the blood incoming side (A side) of the blood circuit and the catheter of the artery were connected to replace the filling fluid (physiological saline) in the set artificial kidney module on the blood side with blood. In the meantime, the blood outgoing side (V side) of the blood circuit was kept opening. The pump was stopped simultaneously with completion of the replacement and a connector on the V side was connected to the catheter on the vein side. The pump was actuated again (restarting was done swiftly after stopping the pump and in this connection, the pump stopped time was about 10 seconds) to start circulation. The flow rate of blood circulation was set at 200 ml/min. The pump on the dialyzing fluid side was actuated after completing blood collection at five minutes after starting circulation to start dialysis. A pump for fluid replacement was adjusted so that the hematocrit during extracorporeal circulation became within 38±6%.

(4) Measurement

For measurement of the blood circulating pressure, a manometer was provided in a circuit between the blood pump and the blood port on the blood incoming side, and pressure was recorded at each point of 1, 5, 15, 30, 60, 120, 180, and 240 minutes after starting circulation in (3).

(Preparation of a Hollow Fiber Module (Module (0)))

5 parts by weight of iso-PMMA and 20 parts by weight of syn-PMMA of weight section 20 were added to 75 parts by weight of dimethyl sulfoxide to obtain an undiluted solution for film production after stirring at 110° C. for eight hours. The undiluted solution for film production was discharged from an orifice type double cylindrical mouthpiece and led to a coagulation bath of 100% water after being passed through the air for 300 mm to obtain a hollow fiber. Dry nitrogen was used as an internal injection gas. The inside diameter of the obtained hollow fiber was 0.2 mm and the thickness thereof was 0.03 mm.

Figure 1:
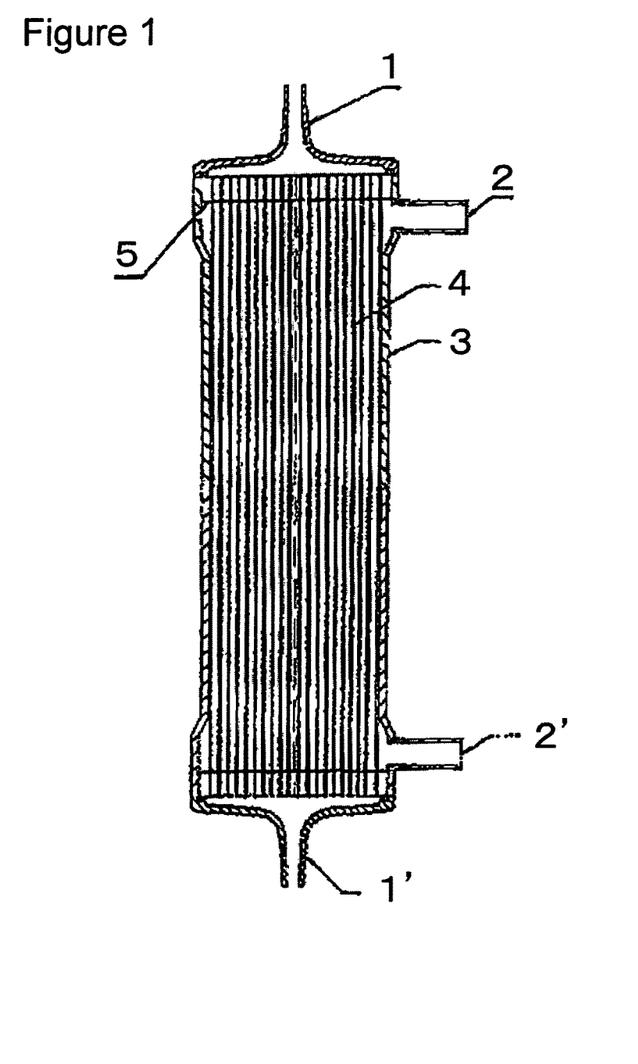
FIG. 1 is a schematic side view exemplifying a hollow fiber module of Examples 1 and 2 and Comparative Examples 1 and 2 of the present invention.

FIG. 1 is a schematic side view exemplifying a hollow fiber module. 11000 PMMA hollow fibers 4 prepared as described above were bundled, and both ends thereof were fixed to a module case 3 by using a urethane potting agent 5 in such a way that a hollow portion was not blocked off to create a hollow fiber module with a structure shown in FIG. 1. An effective area thereof was 1.3 $m^2$. Like a general hollow fiber type dialyzer, the module has two ports (blood ports 1) passing to an inner part of the hollow fiber and two ports (dialyzing fluid ports 2) passing to the outside. Hollow fibers of the hollow fiber module and the inside of the module were cleaned using distilled water to obtain the hollow fiber module (module (0)).

(Preparation of a Buffer)

A buffer of pH 5 was prepared by dissolving Bis-Tris (available from Dojindo Laboratories) and sodium chloride (available from Sigma Aldrich) in ultrapure water in such a way that the concentrations became 0.05 M and 0.1 M respectively, so as to obtain a solution of pH 5 while dropping 6N hydrochloric acid (available from Sigma Aldrich). The glass electrode method was used for pH measurement and a pH meter of Custany LAB F-22 manufactured by HORIBA was used for measurement. As a result, pH was 5.0. An acetate buffer was also prepared as another buffer of pH 5. The acetate buffer was prepared by dissolving acetic acid and sodium acetate in ultrapure water (final concentrations were 0.05 M and 0.1 M respectively). A result of measurement of pH according to the same technique described above yielded 5.0.

Buffers of pH 7.8 and 10 were prepared by dissolving Tris (available from Katayama Chemical Industries Co., Ltd.) and sodium chloride (available from Sigma Aldrich) in ultrapure water in such a way that the concentrations became 0.05 M and 0.1M respectively, so as to obtain solutions of each pH while dropping 6N hydrochloric acid (available from Sigma Aldrich). The same method as that for the buffer of pH 5 was used for measurement of pH. As a result, pH of each buffer was 7.8 and 10.0.

Example 1

A solution (solution A) obtained by dissolving the compound A and a compound B, being a copolymer (F-3031 (lot. 410104) available from Shin-Etsu Chemical Co., Ltd.) of polyether and polysiloxane, in a Tris buffer of pH 7.8 in such a way that the concentrations thereof were as listed in Table 1 was prepared and 0.5 L of the solution A entered at a flow rate of 160 ml/min from the one blood port 1 inside the hollow fibers 4 of the module (0) and exited from the other blood port 1 after passing through the hollow fibers 4, and entered to the dialyzing fluid port 2' on the blood port 1' side via a tube (not shown) and exited to the other dialyzing fluid port 2 (hereinafter, this sequence is referred to as "Sequence 1") to circulate for 15 min. Subsequently, physiological saline entered at a flow rate of 100 ml/min by a pump from the one blood port 1 inside the hollow fibers 4 and reached to the dialyzing fluid port 2' for 75 min to obtain a module (1).

The module (1) was used for a swine extracorporeal circulation experiment. Table 2 shows experiment results of circulating pressure. No pressure rise was observed in 240 minutes after starting circulation.

Example 2

A solution (solution B) was prepared under the same conditions as in Example 1 except that the compound A, the compound B and IPA (code 10982-7 available from Aldrich) were dissolved in such a way that the concentrations thereof were as listed in Table 1, and 2 L of the solution B was circulated at a flow rate of 500 ml/min through the module (0) by the pump in Sequence 1 for 15 min. Next, the module (0) was irradiated with γ ray while ports at four locations were sealed up. The absorbed dose of γ ray was 26 kGy. The inside of the module was cleaned in the following way: 5 L of aqueous solution of 0.025 vol % of polyoxyethylene octylphenylether (Code 30-5140-5 manufactured by Sigma Aldrich (hereinafter, referred to as TritonX-100)) at 25° C. was circulated at a flow rate of 500 ml/min by the pump in Sequence 1 for four hours for cleaning. Then, similarly cleaning was again performed by 5 L of an aqueous solution of 0.025 vol % of TritonX-100 for four hours. Subsequently, 50 L of ultrapure water at 25° C. was circulated at a flow rate of 500 ml/min in Sequence 1. Then, physiological saline entered at a flow rate of 100 ml/min by the pump from the one blood port 1 inside the hollow fibers 4 and reached to the dialyzing fluid port 2' for 75 min to obtain a module (2).

The module (2) was used for a swine extracorporeal circulation experiment. Table 2 shows experiment results. No pressure rise was observed in 240 minutes after starting circulation.

Comparative Example 1

A module (3) was obtained by the same method as that of Example 1 except that the concentration of the compound B in the solution A in Example 1 was 0 ppm by weight. The module (3) was used for a swine extracorporeal circulation experiment. Table 2 shows experiment results. A rise in circulating pressure was observed 60 minutes after starting circulation, which reached 49.3 kPa in 240 minutes after starting circulation.

Comparative Example 2

The module (0) was used for a swine extracorporeal circulation experiment. Table 2 shows experiment results. A rise in circulating pressure was observed 60 minutes after starting circulation, which reached 65.1 kPa in 155 minutes after starting circulation. Immediately thereafter, circulation became impossible and the pump was stopped.

TABLE 1

| | Concentration of IPA (% by volume) | Concentration of Compound A (ppm by weight) | (kPa) Concentration of Compound B (ppm by weight) |
|---|---|---|---|
| Example 1 | — | 30 | 30 |
| Example 2 | 10 | 100 | 100 |
| Comparative Example 1 | — | 30 | 0 |
| Comparative Example 2 | — | 0 | 0 |

TABLE 2

| Circulating time (min) | Example 1 | Example 2 | Comparative Example 1 | (kPa) Comparative Example 2 |
|---|---|---|---|---|
| 1 | 23.5 | 27.5 | 30.9 | 25.9 |
| 5 | 21.6 | 27.3 | 28.0 | 28.0 |
| 15 | 22.4 | 27.5 | 26.8 | 29.5 |
| 30 | 26.3 | 27.7 | 27.9 | 31.6 |

TABLE 2-continued

| Circulating time (min) | Example 1 | Example 2 | Comparative Example 1 | (kPa) Comparative Example 2 |
|---|---|---|---|---|
| 60 | 23.6 | 27.9 | 28.5 | 30.4 |
| 120 | 23.7 | 29.1 | 38.7 | 36.7 |
| 180 | 24.8 | 30.1 | 46.7 | 1) 65.1 |
| 240 | 25.1 | 30.3 | 49.3 | — |

1) Value at circulating time 155 min

Example 3

(1) Creation of Base Material

A solution of 18 parts by weight of PSf ("Udel" P-3500 available from Teijin Amoco), 6 parts by weight of PVP (K90 available from BASF), 3 parts by weight of PVP (K30 available from BASF), 72 parts by weight of N,N-dimethyl acetamide (hereinafter, referred to as DMAc), and 1 part by weight of water was prepared. Subsequently, the solution was applied to glass plates sandwiching a spacer of thickness 0.1 mm and spread like a film by a doctor blade and then, immediately the glass plates were dipped in a solution prepared to 52 parts by weight of DMAc and 48 parts by weight of water to solidify the film, the film was solidified and peeled off the glass plates to obtain as a base material.

(2) Treatment Method of Immobilizing the Compound A and Compound B

The solution as the solution B in Example 2 was prepared, and 5 ml thereof was dispensed into each 15 ml centrifugation tube (manufactured by IWAKI). The base material created in (1) was rolled up and inserted into the centrifugation tube in such a way that the surface thereof was not overlapped. The centrifugation tube was irradiated with γ ray while being kept in a standing position so that the base material was dipped in the solution B. At this point, the irradiation dose was 25 kGy. The base material after radiation irradiation was cleaned by a solution of 0.025 vol % of TritonX-100, being a surface active agent, by ultrapure water and then, by physiological saline until bubbles of the surface active agent disappeared completely.

(3) Evaluation Method 1 ml of physiological saline was added to each well of a 24-well multi-plate (manufactured by Sumitomo Bakelite Co., Ltd.). The base material treated in (2) was cut into square films measuring 1 cm in side and three films as a whole were put into the wells, one film per well. Next, immediately after moving the base material into an empty well, human whole blood was collected from a volunteer, 1 ml of the blood was added to each well and the multi-plate was shaken. After a predetermined time (because of an individual difference, the time was not standardized, a well of blood without the base material was prepared, and the time when clearly viscosity appeared was defined as a blood immersion time) as the blood immersion time passes, the base material was taken out and gently cleaned twice by new physiological saline. The base material after cleaning was observed visually and the degree of coagulation was evaluated on a scale of 1 to 5 depending on the degree of attachment of blood clot to calculate an average value. The average value was determined by rounding off a value to the nearest integer. The degree of coagulation was represented ranging from 1 (completely free from blood clot) through 3 (blood clots were attached to about half the area of the base material) to 5 (blood clots were attached overall). Score 2 indicates that blood clots are attached to about one fourth of the area of the base material and Score 4 indicates that blood clots are attached to about three fourths of the area of the base material. In a case where a blood clot attached state was such that no score applies, the state was counted as a score of the nearest state to determine the score of each base material. As a result, the score was 1.

Comparative Example 3

A base material was created under the same conditions as those of Example 3 except that the compound A was not immobilized in (2) of Example 3, and the score was 4 as a result of evaluation in the same manner as in (3) of Example 3.

Comparative Example 4

A base material was created under the same conditions as those of Example 3 except that the compound B was not immobilized in (2) of Example 3, and the score was 3 as a result of evaluation in the same manner as in (3) of Example 3.

Comparative Example 5

A base material was created under the same conditions as those of Example 3 except that the compounds A and B were not immobilized in (2) of Example 3, and the score was 5 as a result of evaluation in the same manner as in (3) of Example 3.

(Measurement of the Antithrombin Activity Value)

As an index showing antithrombin activity, the residual ratio of the antithrombin activity value after radiation irradiation was used. For measurement of the antithrombin activity value, an ECA-T kit available from HaemoSys was used as a reagent and COATRON M1 (code 80 800 000) manufactured by TECO Medical Instruments Production was used as an apparatus. First, 20 μl of the solution to be measured was added to 80 μl of human plasma (Human Plasma 12271210, lot. 16878 marketed by Cosmo Bio Co., Ltd.) and stirred. The solution is defined as a sample solution. The sample solution was cooled in an ice bath immediately before measurement. 100 μl of ECA prothrombin buffer, 30 μl of the sample solution, and 25 μl of ECA-T substrate were mixed and incubated at 37° C. for 60 seconds before being set to the apparatus. 50 μl of ECA ecarin reagent was added to this before measurement. A sample prepared by using ultrapure water was measured as a blank measurement target solution. The residual ratio was determined by the following formula (1):

$$A = 100 \times (B-D)/(C-D) \qquad \text{formula (1)}$$

In the above formula (1), symbols are defined as follows:
A: Residual ratio of antithrombin activity (%)
B: Sample measured value after radiation irradiation (sec.)
C: Sample measured value before radiation irradiation (sec.)
D: Blank measured value (sec.)

Reference Examples 1 to 3

Figure 3:
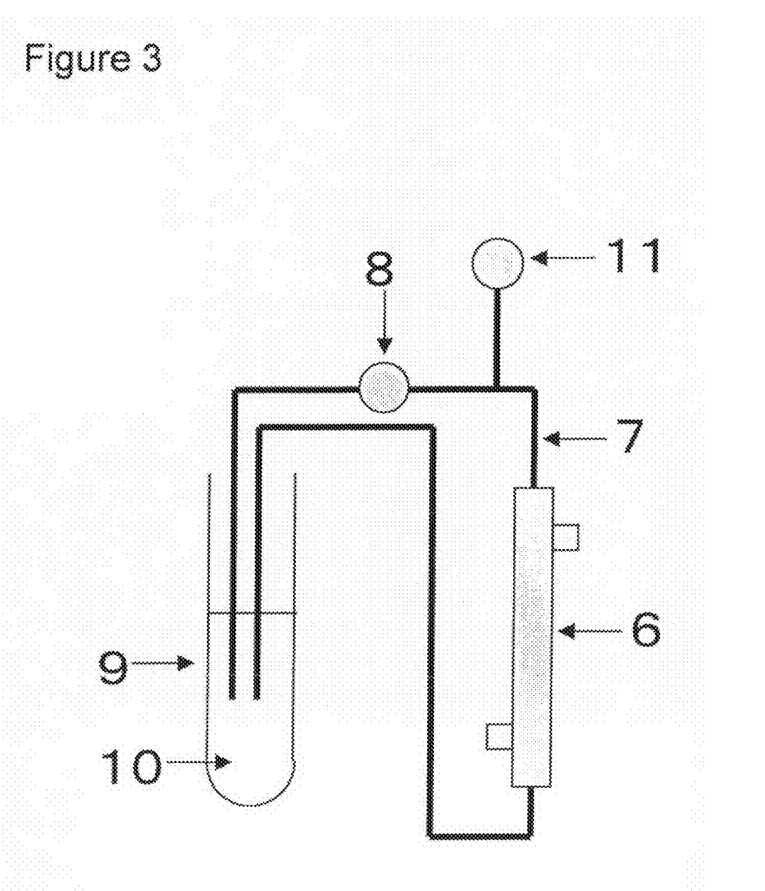
FIG. 3 is a schematic system diagram exemplifying a circuit used for a circulation test of Examples 12 to 14 and Comparative Examples 10 to 12 of the present invention.

An IPA solution was prepared by dissolving IPA (available from Sigma Aldrich) in ultrapure water in such a way that the concentration became as listed in Table 3. The compound A was dissolved in this solution in such a way that the concentration thereof was 5000 ppm by weight to prepare a solution, which was irradiated with γ rays. The absorbed dose of γ ray was 25 kGy. The antithrombin activity values of the solution before and after radiation irradiation were measured and the residual ratio of the antithrombin activity value was calculated according to the above formula (1). A result of which is shown in FIG. 3.

Reference Example 4

An experiment was performed under the same conditions as those of Reference Example 1 except that a glycerin solution was prepared by using glycerin (available from Sigma Aldrich), instead of IPA, and the residual ratio of the antithrombin activity value was calculated according to the above formula (1). A result of which is shown in FIG. 3.

Reference Example 5

An experiment was performed under the same conditions as those of Reference Example 1 except that a PG solution was prepared by using PG (available from Wako Pure Chemical Industries, Ltd.) instead of IPA, and the residual ratio of the antithrombin activity value was calculated according to the above formula (1). A result of which is shown in FIG. 3.

Comparative Reference Example 1

An experiment was performed under the same conditions as those of Reference Example 1 except that a compound A solution with a concentration of 5000 ppm by weight was prepared by dissolving the compound A used in Example 1, and the residual ratio of the antithrombin activity value was calculated according to the above formula (1). A result of which is shown in FIG. 3.

Comparative Reference Example 2

An experiment was performed under the same conditions as those of Reference Example 1 except that an EG solution was prepared by using EG (available from Sigma Aldrich) instead of IPA, and the residual ratio of the antithrombin activity value was calculated according to the above formula (1). A result of which was shown in FIG. 3.

Comparative Reference Example 3

An experiment was performed under the same conditions as those of Reference Example 1 except that a PEG solution was prepared by using PEG (available from Nacalai Tesque, Inc.) instead of IPA, and the residual ratio of the antithrombin activity value was calculated according to the above formula (1). A result of which was shown in FIG. 3.

TABLE 3

| | organic solvent | concentration of organic solvent (% by volume) | Residual ratio of antithrombin activity (%) |
|---|---|---|---|
| Reference Example 1 | IPA | 75 | 79.4 |
| Reference Example 2 | IPA | 50 | 61.4 |
| Reference Example 3 | IPA | 10 | 33 |
| Reference Example 4 | glycerin | 50 | 53.8 |
| Reference Example 5 | PG | 10 | 64 |
| Comparative Reference Example 1 | — | 0 | 0 |
| Comparative Reference Example 2 | EG | 50 | 8.3 |
| Comparative Reference Example 3 | PG | 50 | 6.9 |

Example 4

A compound A aqueous solution with a concentration of 5000 ppm by weight was prepared by dissolving the compound A in ultrapure water. The compound A aqueous solution, ultrapure water, IPA, and a Bis-Tris buffer of pH 5 in double concentration were mixed in such a way that the concentrations became as listed in Table 4. The compound A buffer was irradiated with γ ray. The absorbed dose of γ ray was 25 kGy. The antithrombin activity values of the compound A buffer before and after radiation irradiation were measured and the residual ratio of the antithrombin activity values was calculated according to the above formula (1). As a result, the residual ratio of the antithrombin activity values when the IPA fractions are 0.1, 1, 10, and 50 vol % are as listed in Table 4.

Example 5

A compound A aqueous solution was prepared in the same manner as in Example 4. The compound A aqueous solution, ultrapure water, IPA, and an acetate buffer of pH 5 in double concentration were mixed in such a way that the concentrations became as listed in Table 4. The compound A buffer was irradiated with γ ray by the same method as in Example 4. The antithrombin activity values of the compound A buffer before and after radiation irradiation were measured and the residual ratio of the antithrombin activity values was calculated according to the above formula (1). As a result, the residual ratio of the antithrombin activity values when the IPA fractions are 0.1, 1, 10, and 50 vol % are as listed in Table 4.

Example 6

A compound A aqueous solution was prepared in the same manner as in Example 4. The compound A aqueous solution, ultrapure water, IPA, and a Tris buffer of pH 7.8 in double concentration were mixed in such a way that the concentrations became as listed in Table 4. The compound A buffer was irradiated with γ ray by the same method as in Example 4. The antithrombin activity values of the compound A buffer before and after radiation irradiation were measured and the residual ratio of the antithrombin activity values was calculated according to the above formula (1). As a result, the residual ratio of the antithrombin activity values when the IPA fractions are 0.1, 1, 10, and 50 vol % are as listed in Table 4.

Comparative Example 6

A compound A aqueous solution was prepared in the same manner as in Example 4. The compound A aqueous solution, ultrapure water, IPA, and a Tris buffer of pH 10 in double concentration were mixed in such a way that the concentrations became as listed in Table 4. The compound A buffer was irradiated with γ ray by the same method as in Example 4. The antithrombin activity values of the compound A buffer before and after radiation irradiation were measured and the residual ratio of the antithrombin activity values was calculated according to the above formula (1). As a result, the residual ratio of the antithrombin activity values when the IPA fractions are 0.1, 1, 10, and 50 vol % are as listed in Table 4.

TABLE 4

|  | pH | buffer | Concentration of IPA (% by volume) | Residual ratio of antithrombin activity (%) |
|---|---|---|---|---|
| Example 4 | 5 | Bis-Tris | 0.1 | 15.3 |
|  |  |  | 1 | 19.4 |
|  |  |  | 10 | 37.8 |
|  |  |  | 50 | 76.8 |
| Example 5 | 5 | acetate | 0.1 | 0 |
|  |  |  | 1 | 2.0 |
|  |  |  | 10 | 6.5 |
|  |  |  | 50 | 52.1 |
| Example 6 | 7.8 | Tris | 0.1 | 12.9 |
|  |  |  | 1 | 13.6 |
|  |  |  | 10 | 17.6 |
|  |  |  | 50 | 66.4 |
| Comparative Example 6 | 10 | Tris | 0.1 | 2.1 |
|  |  |  | 1 | 2.4 |
|  |  |  | 10 | 1.5 |
|  |  |  | 50 | 4.8 |

[Preparation Method of a PMMA Hollow Fiber Mini-Module]

50 PMMA hollow fibers prepared by the creation method of the module (0) were bundled. Both ends thereof were fixed to a module case by using an epoxy potting agent while taking care so that a hollow portion of the hollow fibers was not blocked off to create a mini-module (FIG. 2) shown in FIG. 2 (the work of this sentence is referred to as Sequence 2). The diameter of the mini-module is about 7 mm and the length thereof is about 12 cm. Like a general hollow fiber type dialyzer, the mini-module has two ports (blood ports) passing to an inner part of the hollow fiber and two ports (dialyzing fluid ports) passing to the outside. Hollow fibers of the mini-module and the inside of the mini-module were cleaned using distilled water.

[Preparation Method of a PSf Hollow Fiber Mini-Module]

18 parts by weight of PSf (Udel (registered trademark) P-3500 available from Solvay) and 9 parts by weight of PVP (K30 available from BASF) were added to a mixed solvent of 72 parts by weight of DMAc and 1 part by weight of water to obtain an undiluted solution for film production after heating at 90° C. for 14 hours for dissolution. The undiluted solution for film production was discharged from an outer pipe of an orifice type double cylindrical mouthpiece (outside diameter: 0.3 mm; inside diameter: 0.2 mm) in an annular slit. A solution including 58 parts by weight of DMAc and 42 parts by weight of water was discharged from an inner pipe in the same manner as a core liquid. The discharged undiluted solution for film production passed the distance for 350 mm from the mouthpiece to the surface of a coagulation bath through the air before being led to the coagulation bath of 100% water, resulting in obtaining a hollow fiber film. 50 PSf hollow fibers prepared in this manner were bundled to create a mini-module according to Sequence 2. Outside dimensions and ports are the same as those of the aforementioned PMMA hollow fiber mini-module. The hollow fiber film of the mini-module and the inside of the mini-module were cleaned using distilled water.

[Eluted Substances Confirmation Method]

Eluted substances into blood were confirmed in the following way: the compound A was dissolved in distilled water to prepare a compound A aqueous solution with a predetermined concentration and the compound A aqueous solution was passed to the mini-module at a predetermined flow rate and irradiated with γ ray. A concrete procedure for passing the compound A aqueous solution to the mini-module will be described later in each Example and Comparative Example. FIG. 3 shows a schematic system diagram of a circuit used to pass a compound A aqueous solution.

In FIG. 3, a silicon tube 7 (inside diameter: 0.8 mm; length: 52 cm) was connected to one blood port of a mini-module 6, and a peristaltic pump 8 and a manometer 11 (AP-32A manufactured by Keyence Corporation) were provided midway through the circuit. A silicon tube (inside diameter: 0.8 mm; length: 16 cm) was connected to the other blood port. The other side of each of both silicon tubes not connected to the blood port was inserted into a 5 ml polystyrene round tube 9 (Code: 352054) manufactured by BECTON DICKINSON to make a circulation circuit.

Next, after the cleaning method shown in each Example or Comparative Example was performed, the circuit was used to perform a blood circulation experiment according to a method shown below: 5 ml of human plasma (reference numeral 10 in FIG. 2) was added from the polystyrene round tube 9 and the silicon tubes were inserted into the blood ports to send a liquid at a flow rate of 0.5 ml/min adjusted by the peristaltic pump 8 for four-hour circulation after discarding the amount of liquid for the first two minutes. The concentration of the compound A eluted in plasma after the circulation was measured by an ECA-T kit.

Example 7

5.8 ml of an aqueous solution containing the compound A and the compound B (each concentration was 6 ppm and pH of the Tris buffer was 8.0 only in this case) was introduced at a flow rate of 0.7 ml/min by the peristaltic pump into one blood port of the PMMA hollow fiber mini-module to pass the solution to the other blood port, and after discarding the initial 1.4 ml, the circulation continued for 15 minutes. Subsequently, physiological saline was introduced at a flow rate of 0.46 ml/min from one blood port of the PMMA hollow fiber mini-module and exited from the other blood port after passing through the hollow fibers and then, introduced into the dialyzing fluid port on the blood port side via a silicon tube and discharged from the other dialyzing fluid port for 37 minutes. 5.8 ml of a compound A aqueous solution of 6 ppm by weight at flow rate of 0.7 ml/min by the peristaltic pump was introduced from one blood port of the PMMA hollow fiber mini-module to exit from the other blood port after passing through the hollow fibers and then, introduced into the dialyzing fluid port on the blood port side via the silicon tube and discharged from the other dialyzing fluid port. After being cleaned by physiological saline, the mini-module was irradiated with γ ray while ports at four locations were sealed up. The absorbed dose of γ ray was 25 kGy. The hollow fiber separation film of the mini-module and the inside of the mini-module were cleaned by passing a solution of 0.025% by weight of TritonX-100 at 25° C. at a flow rate of 10 ml/min for four hours by using the peristaltic pump. The hollow fiber separation film of the mini-module and the inside of the mini-module were cleaned again by using a newly prepared solution of TritonX-100 under the same conditions for four hours. Subsequently, the hollow fibers of the mini-module and the inside of the mini-module were cleaned by passing 300 ml of each of distilled water and physiological saline at 25° C. by using the peristaltic pump at a flow rate of 10 ml/min to obtain a hollow fiber mini-module (hereinafter, abbreviated as a mini-module (1)). Distilled water cleaning and physiological saline cleaning do not occur at the same time.

Measurement of the amount of elution of the compound A in the mini-module (1) showed 0 μg/ml.

Example 8

30 ml of an aqueous solution containing the compound A and the compound B (each concentration was 100 ppm) was introduced at a flow rate of 1 ml/min by the peristaltic pump from one blood port of the PSf hollow fiber mini-module to pass the solution to the other blood port and the circulation continued for 15 minutes. Subsequently, 30 ml of a newly prepared aqueous solution containing the compound A and the compound B (each concentration was 100 ppm) was passed out of the other blood port after passing through the hollow fibers and then, introduced into the dialyzing fluid port on the blood port side via a silicon tube to be passed to the other dialyzing fluid port and this circulation continued for 15 minutes. Subsequently, the mini-module was irradiated with γ ray under the same conditions as those in Example 7. Next, the hollow fibers of the mini-module and the inside of the mini-module were cleaned by the same method and under the same conditions as those in Example 7 to obtain a mini-module (2).

Measurement of the amount of elution of the compound A in the mini-module (2) showed 0 μg/ml.

Comparative Example 7

A mini-module (3) was obtained by the same method as that in Example 7 until before irradiation with γ ray except that the mini-module was not irradiated with γ ray.

Measurement of the amount of elution of the compound A in the mini-module (3) showed 3.5 μg/ml.

Comparative Example 8

15 ml of an aqueous solution containing the compound A and the compound B (each concentration was 100 ppm) was introduced at a flow rate of 1 ml/min by the peristaltic pump from one blood port of the PSf hollow fiber mini-module to pass the solution by the same method as in Example 8 and the circulation continued for 15 minutes. Subsequently, the mini-module was irradiated with γ ray under the same conditions as those in Example 7. Distilled water at 25° C. was passed at a flow rate of 10 ml/min by using the peristaltic pump to clean the hollow fibers of the mini-module and the inside of the mini-module for two hours. Subsequently, 300 ml of physiological saline at 25° C. was passed at a flow rate of 10 ml/min by using the peristaltic pump to clean the hollow fibers of the mini-module and the inside of the mini-module to obtain a mini-module (4).

Measurement of the amount of elution of the compound A in the mini-module (4) showed 4.7 μg/ml.

[Measurement of Thrombin Adsorption Amount]

Figure 2:
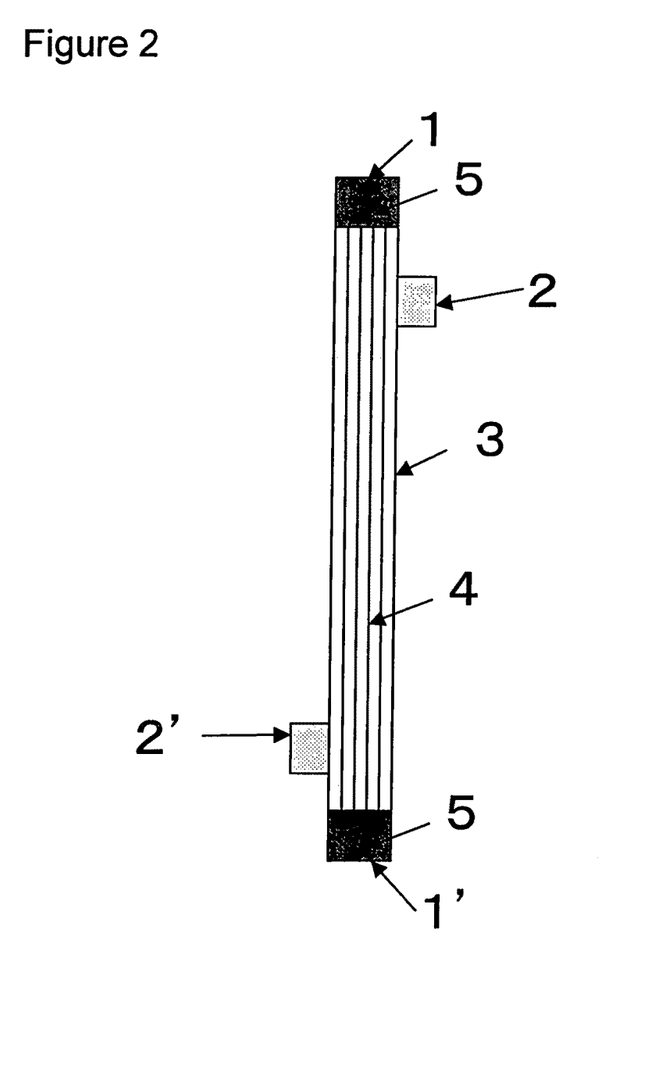
FIG. 2 is a schematic side view exemplifying a hollow fiber mini-module of Examples 12 to 14 and Comparative Examples 10 to 12 of the present invention.

The mini-module (1) and an untreated PMMA hollow fiber mini-module were created and set like in a circuit obtained by removing the manometer 11 in FIG. 2. After physiological saline was sent at a flow rate of 0.5 ml/min to remove bubbles, 5 ml of a protein solution (thrombin (HCT-0020 Lot T0326-1MG available from Technologies Inc.) and fetal bovine serum albumin (BSA (A-7906 (Lot# 41K1270) available from SIGMA)) were dissolved in physiological saline in such a way that the final concentrations became 0.35 and 75 μg/ml respectively and the whole volume was prepared to 27 ml) were sent to Eiken tube No. 1. The initial 1.8 ml after starting to send the solution was discarded and the circulation continued for four hours. Plasma after the circulation was collected as a sample and the amount of thrombin was measured by the ELISA method described below.

An antithrombin antibody (AHT-5020 LotS0429-01MG available from Haematologic Technologies Inc.) as a primary antibody was dissolved in a solution (9.6 g of PBS(−) (05913 (Lot137311) available from Nihon Pharmaceutical Co., Ltd.) was measured up to 1 L by distilled water) and prepared to the concentration of 0.1 ng/ml. 100 μl of this solution was added to each well of a 96-well ELISA plate (MS-8596F available from Sumitomo Bakelite Co., Ltd.) and left alone at room temperature for 60 minutes. The solution was thrown away by a method generally applied in ELISA and 400 μl of a blocking liquid (0.25 g of BSA was dissolved in PBS (−) and prepared to the concentration of 0.5% by weight) was added to each well and left alone for 20 minutes. The plate was cleaned by PBS (−) -T (810 ml of PBS (−) and 405 μl of 162-21112 (LotASP7153) available from Wako) four times. Subsequently, 100 μl of standard thrombin (HCT-0020 LotT0326-1MG available from Haematologic Technologies Inc.) prepared to the concentration for calibration curve based on a sample or diluent (prepared by dissolving 0.125 g of BSA in 50 ml of PBS (−)-T) was added to each well and the plate was shaken slowly for 60 minutes. Subsequently, the plate was cleaned by PBS (−)-T for six times. Further, 100 μl of an antithrombin HRP standard antibody (SAHT-HRP LotAB46-67R2 available from Bilogical Inc.) solution diluted 5000 times by a diluent as a secondary antibody was added to each well and after the plate being slowly shaken at room temperature for 30 minutes, the plate was cleaned by PBS (−) -T for six times. Subsequently, 100 μl of TMB one solution (G7431 (Lot18729904) available from Promega) was added to each well, the plate was shaken slowly for 10 minutes, 100 μl of 1 N HCl (420-00055 available from Hayashi Pure Chemical Ind. Ltd.) was added to each well to stop reaction. Immediately after the reaction stops, a micro-plate reader (MPR-A4iII manufactured by TOSOH) was used to measure absorbance at the wavelength 450 nm (600 nm was used as a reference wavelength).

Example 9

As a result of measuring thrombin adsorption amount in the mini-module (1), the adsorption amount was 4.0 ng/cm$^2$.

Comparative Example 9

As a result of measuring thrombin adsorption amount in an untreated PMMA hollow fiber mini-module, the adsorption amount was 0.5 ng/cm$^2$.

The invention claimed is:

1. A manufacturing method of a substrate, comprising contacting a substrate with a compound having blood anticoagulation activity and a hydrophilic polymer compound,
    irradiating the substrate with radiation in the presence of a tris-hydroxymethyl-aminomethane buffer and/or a bis (2-hydroxyethyl) imino trio (hydroxymethyl) methane buffer having a pH of from 3 to 10, and an organic solvent solution satisfying following conditions A and B:
    A: moisture content of from 25% by volume to 90% by volume;

B: at least one secondary or tertiary hydroxyl group is contained, and washing the substrate to remove unreacted components.

2. The manufacturing method of a substrate according to claim 1, wherein the substrate is washed with a surface active agent.

* * * * *